United States Patent [19]
Rogers et al.

[11] Patent Number: 5,985,871
[45] Date of Patent: Nov. 16, 1999

[54] BENZOXAZINE COMPOUNDS FOR ENHANCING SYNAPTIC RESPONSE

[75] Inventors: Gary A. Rogers, Santa Barbara; Christopher Marrs, Foothill Ranch, both of Calif.

[73] Assignee: Cortex Pharmaceuticals, Inc., Irvine, Calif.

[21] Appl. No.: 08/998,300

[22] Filed: Dec. 24, 1997

[51] Int. Cl.$^6$ ............... A61K 31/535; C07D 498/04; C07D 498/14
[52] U.S. Cl. ............... 514/229.5; 514/211; 514/222.8; 514/230.2; 540/468; 540/471; 540/546; 540/548; 540/555; 540/559; 544/14; 544/32; 544/73; 544/95
[58] Field of Search ............... 544/95, 14, 32, 544/73; 514/229.5, 230.2, 211, 222.8; 540/468, 471, 546, 548, 555, 559

[56] References Cited

U.S. PATENT DOCUMENTS

| | | | |
|---|---|---|---|
| 5,650,409 | 7/1997 | Rogers et al. | 514/230.2 |
| 5,736,543 | 4/1998 | Rogers et al. | 514/229.5 |

FOREIGN PATENT DOCUMENTS

| | | |
|---|---|---|
| WO 94/02475 | 2/1994 | WIPO . |
| WO 96/38414 | 12/1996 | WIPO . |
| WO 97/36907 | 10/1997 | WIPO . |

OTHER PUBLICATIONS

Kapor et al., Chemical Abstracts, vol. 122, abstract 119629, 1995.
Ziegler et al., Chemical Abstracts, vol. 70, abstract 3979, 1969.

*Primary Examiner*—Richard L. Raymond
*Attorney, Agent, or Firm*—Vincent M. Powers

[57] ABSTRACT

Compounds having a certain benzoxazine ring system and their precursors are disclosed which are useful for enhancing synaptic responses mediated by AMPA receptors. Also disclosed are methods for preparing such compounds, and methods for their use in treating subjects suffering from impaired nervous or intellectual functioning due to deficiencies in the number of excitatory synapses or in the number of AMPA receptors. The invention compounds can also be used for the treatment of non-impaired subjects for enhancing performance in sensory-motor and cognitive tasks which depend on brain networks utilizing AMPA receptors and for improving memory encoding.

41 Claims, 1 Drawing Sheet

BENZOXAZINE COMPOUNDS FOR ENHANCING SYNAPTIC RESPONSE

FIELD OF THE INVENTION

This invention relates to benzoxazine compounds useful for the prevention and treatment of cerebral insufficiency, including enhancement of receptor functioning in synapses in brain networks responsible for higher order behaviors. In particular, the invention relates to compounds that are useful for treatment of schizophrenia, related psychoses, and depression, and for enhancing the strength of memory in mammals, particularly humans.

BACKGROUND OF THE INVENTION

The release of glutamate at synapses at many sites in mammalian forebrain stimulates two classes of postsynaptic receptors. These classes are usually referred to as AMPA/quisqualate and N-methyl-D-aspartic acid (NMDA) receptors. AMPA/quisqualate receptors mediate a voltage independent fast excitatory post-synaptic current (the fast epsc) whereas NMDA receptors generate a voltage-dependent, slow excitatory current. Studies carried out in slices of hippocampus or cortex indicate that the AMPA receptor-mediated fast epsc is by far the dominant component at most glutamatergic synapses under most circumstances.

AMPA receptors are not evenly distributed across the brain but instead are largely restricted to telencephalon and cerebellum. These receptors are found in high concentrations in the superficial layers of neocortex, in each of the major synaptic zones of hippocampus, and in the striatal complex, as reported by Monaghan et al., in *Brain Research* 324:160–164 (1984). Studies in animals and humans indicate that these structures organize complex perceptual-motor processes and provide the substrates for higher-order behaviors. Thus, AMPA receptors mediate transmission in those brain networks responsible for a host of cognitive activities.

For the reasons set forth above, drugs that enhance the functioning of AMPA receptors offer significant benefits for intellectual performance. Such drugs should also facilitate memory encoding. Experimental studies, such as those reported by Arai and Lynch, *Brain Research*, 598:173–184 (1992), indicate that increasing the size of AMPA receptor-mediated synaptic response(s) enhances the induction of long-term potentiation (LTP). LTP is a stable increase in the strength of synaptic contacts that follows repetitive physiological activity of a type known to occur in the brain during learning. Compounds that enhance the functioning of AMPA-type glutamate receptors facilitate the induction of LTP and the acquisition of learned tasks as measured by a number of paradigms. Granger et al., *Synapse* 15:326–329 (1993); Staubli et al., *PNAS* 91:777–781 (1994); Arai et al., *Brain Res.* 638:343–346 (1994); Staubli et al., *PNAS* 91:11158–1162 (1994); Shors et al., *Neurosci. Let.* 186:153–156 (1995); Larson et al., *J. Neurosci.* 15:8023–8030 (1995); Granger et al., *Synapse* 22:332–337 (1996); Arai, et al., *JPET* 278:627–638 (1996); Lynch et al., *Internat. Clin. Psychopharm.* 11:13–19 (1996); Lynch et al., *Exp. Neurology* 145:89–92 (1997); Ingvar et al., *Exp. Neurology* 146:553–559 (1997); and International Patent Application Publication No. WO 94/02475.

There is a considerable body of evidence showing that LTP is the substrate of memory. For example, compounds that block LTP interfere with memory formation in animals, and certain drugs that disrupt learning in humans antagonize the stabilization of LTP, as reported by del Cerro and Lynch, *Neuroscience* 49:1–6 (1992). A possible prototype for a compound that selectively facilitates the AMPA receptor was disclosed by Ito et al., *J. Physiol.* 424:533–543 (1990). These authors found that the nootropic drug aniracetam (N-anisoyl-2-pyrrolidinone) increases currents mediated by brain AMPA receptors expressed in Xenopus oocytes without affecting responses by γ-aminobutyric acid (GABA), kainic acid (KA), or NMDA receptors. Infusion of aniracetam into slices of hippocampus was also shown to substantially increase the size of fast synaptic potentials without altering resting membrane properties. It has since been confirmed that aniracetam enhances synaptic responses at several sites in hippocampus, and that it has no effect on NMDA-receptor mediated potentials. See, for example, Staubli et al., in *Psychobiology* 18:377–381 (1990) and Xiao et al., *Hippocampus* 1:373–380 (1991). Aniracetam has also been found to have an extremely rapid onset and washout, and can be applied repeatedly with no apparent lasting effects; these are valuable traits for behaviorally-relevant drugs. Unfortunately, the peripheral administration of aniracetam is not likely to influence brain receptors. The drug works only at high concentrations (~1.0 mM) and Guenzi and Zanetti, *J. Chromatogr.* 530:397–406 (1990) report that about 80% of the drug is converted to anisoyl-GABA following peripheral administration in humans. The metabolite, anisoyl-GABA, has been found to have only weak aniracetam-like effects.

Accordingly, there is a need to identify new compounds for use in enhancing synaptic responses, and particularly for treating or alleviating conditions such as depression, schizophrenia, schizophreniform behavior, and other psychotic conditions, drug-dependencies such as addictions to drugs of abuse, and for enhancing memory and other cognitive functions. Such compounds are described below.

SUMMARY OF THE INVENTION

It has now been discovered that synaptic responses mediated by AMPA receptors are increased by administration of a novel class of benzoxazine derivatives described below. The ability of these compounds to increase AMPA receptor-mediated responses makes the compounds useful in serving a variety of purposes, including facilitating the learning of behaviors dependent upon AMPA receptors, and use as therapeutic drugs in conditions in which AMPA receptors or synapses utilizing these receptors are reduced in numbers or efficiency, or in those circumstances when enhanced excitatory synaptic activity would be beneficial.

These and other features and advantages of the invention will become more apparent from the description that follows.

DETAILED DESCRIPTION OF THE INVENTION

Figure 1:
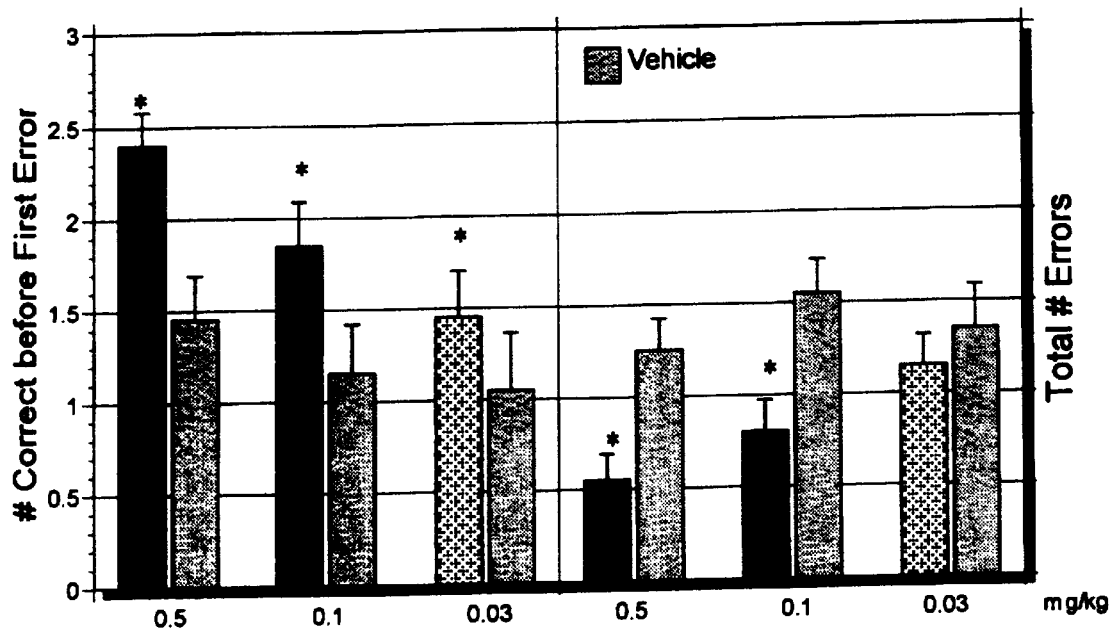
FIG. 1 is a bar graph showing dose-dependence in a memory test involving administration of an exemplary compound in accordance with the present invention.

In one aspect, the present invention includes benzoxazine compounds having the following formula:

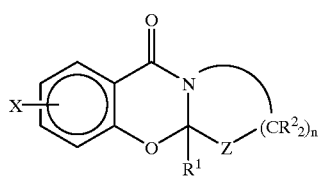

Formula I

In this formula:

X is absent or represents one to four non-hydrogen substituents independently selected from cyano; halogen; hydroxy; amino, alkylamino or dialkylamino ($C_1$–$C_{12}$); nitro; thiol; $C_1$–$C_6$ alkylthio; $C_1$–$C_{12}$ alkyl, alkenyl, or alkynyl; $C_1$–$C_{12}$ alkoxy, alkenoxy, or alkynoxy; $C_1$–$C_{12}$ alkylsulfonamido, alkenylsulfonamido, or alkynylsulfonamido; $C_2$–$C_{12}$ alkylacyl; $C_3$–$C_{12}$ Ar, Aroxy, Aramino, Arthio, Aroxyalkyl, Arsulfonamido, or Aracyl, where Ar represents an aromatic carbocyclic moiety, an aromatic heterocyclic moiety, an aromatic carbocyclic alkyl moiety, or an aromatic heterocyclic alkyl moiety; carboxyl; $C_2$–$C_{12}$ carboxyalkyl; such that any of the preceding carbon-containing groups may be substituted with one or more substituents selected from lower alkyl, lower alkoxy, hydroxy, cyano, halo, amino, alkylamino, and dialkylamino, where alkyl is preferably $C_1$–$C_3$ alkyl or $C_1$–$C_3$ fluoroalkyl; and where the compound contains two adjacent X groups, the two adjacent X groups join together to form a fused alkyl, heteroalkyl, aryl, or heteroaryl ring, as illustrated by the following examples:

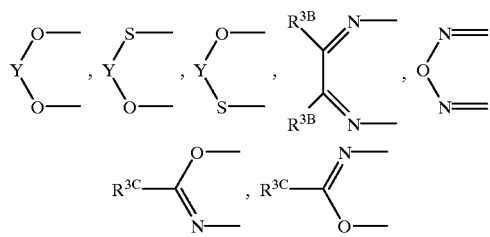

in which:

each occurrence of $R^1$ is independently H, $C_1$–$C_6$ alkyl, or $C_1$–$C_3$ fluoroalkyl, with H and $C_1$–$C_3$ alkyl being preferred;

each occurrence of $R^2$ is independently H, halogen, cyano, hydroxy, $C_1$–$C_6$ alkoxy, $C_1$–$C_3$ fluoroalkoxy, thiol, $C_1$–$C_6$ alkyl, $C_1$–$C_3$ fluoroalkyl, $C_2$–$C_6$ alkoxyalkyl, $C_6$–$C_{12}$ aryl, $C_3$–$C_{12}$ heteroaryl, $C_7$–$C_{12}$ arylalkyl, $C_4$–$C_{12}$ heteroarylalkyl, $C_6$–$C_{12}$ aryloxy, $C_7$–$C_{12}$ aryloxyalkyl, $C_7$–$C_{12}$ arylalkoxy, or $C_4$–$C_{12}$ heteroarylalkoxy, with H, halogen, cyano and alkoxy being preferred, and such that when $R^2$ is hydroxy, thiol, alkoxy, fluoroalkoxy, aryloxy, or arylalkoxy, n is 3 or 4 and such $R^2$ group is not attached to the same carbon as the Z group or the benzoxazine amide nitrogen;

Y is $CR^{3A}_2$, $CR^{3A}_2CR^{3A}_2$ or $CR^{3A}=CR^{3A}$, where each occurrence of $R^{3A}$ is independently H, halogen, cyano, $C_1$–$C_6$ alkyl, $C_1$–$C_3$ fluoroalkyl, $C_2$–$C_6$ alkoxyalkyl, $C_7$–$C_{12}$ arylalkyl, $C_4$–$C_{12}$ heteroarylalkyl, or $C_7$–$C_{12}$ aryloxyalkyl, with H, cyano, $C_1$–$C_3$ alkyl, $C_1$ fluoroalkyl, $C_7$–$C_{10}$ arylalkyl and $C_4$–$C_8$ heteroarylalkyl being preferred, and H, cyano, $C_1$–$C_3$ alkyl, and $C_1$ fluoroalkyl being more preferred;

each occurrence of $R^{3B}$ is independently H, cyano, hydroxy, $C_1$–$C_6$ alkoxy, $C_1$–$C_6$ alkyl, $C_1$–$C_3$ fluoroalkyl, $C_2$–$C_6$ alkoxyalkyl, or $C_7$–$C_{12}$ arylalkyl, $C_4$–$C_{12}$ heteroarylalkyl, $C_6$–$C_{12}$ aryloxy, $C_7$–$C_{12}$ aryloxyalkyl, $C_7$–$C_{12}$ arylalkoxy, or $C_4$–$C_{12}$ heteroarylalkoxy, with H, cyano, alkoxy, $C_1$–$C_3$ alkyl, and $C_1$ fluoroalkyl being preferred;

each occurrence of $R^{3C}$ is independently H, $C_1$–$C_6$ alkyl, or $C_1$–$C_3$ fluoroalkyl;

Z is a heteroatom such as O, $NR^7$, or S;

each occurrence of $R^7$ is independently H, $C_1$–$C_6$ alkyl, $C_1$–$C_3$ fluoroalkyl, $C_7$–$C_{12}$ arylalkyl or $C_4$–$C_{12}$ heteroarylalkyl, with $C_1$–$C_3$ alkyl being preferred; and n is 2, 3, or 4.

Among the compounds defined by the above formula, certain additional subclasses are preferred. Each occurrence of X, which may be the same or different, is preferably alkyl, alkoxy, alkenoxy, alkynoxy, alkoxyalkyl, carboxyalkyl, all containing no more than six carbon atoms, $C_6$–$C_{12}$ aryloxyalkyl (where the alkyl portion of the aryloxyalkyl group is $C_1$–$C_3$), dialkylamino, alkylthio, and alkylacyl, wherein the alkyl groups in the preceding three groups contain no more than six carbon atoms. Preferably, the compound contains one or two X groups. Where there is only one X group, X is preferably $NR^3_2$, $R^4OCH_2$ or $R^4O$, where $R^3$ is as defined below, and $R^4$ is H, $C_1$–$C_6$ alkyl, or $C_1$–$C_3$ fluoroalkyl, and $R^4$ is more preferably $C_1$–$C_3$ alkyl or perfluoro $C_1$–$C_2$ alkyl, with $R^4$=$CH(CH_3)_2$ or $CF_3$ being most preferred. When the compound contains a halogen X group, it is preferred that the compound also contain a second X group that is not a halogen. In another preferred embodiment, the compound contains two adjacent X groups which taken together form a fused ring as exemplified above, with methylenedioxy and ethylenedioxy being preferred.

Alkyl is preferably fluorinated alkyl.

Z is preferably O or S, and more preferably is O.

In a more specific embodiment, the present invention includes compounds having the following structure:

Formula II

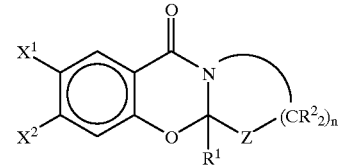

wherein:

$X^1$ and $X^2$ are independently selected from H, $NR^3_2$, —$OR^4$, and —$CH_2OR^4$; or $X^1$ and $X^2$ taken together are —$OCR^5_2O$—, —$OCR^5_2CR^5_2O$—, or —$OCR^5$=$CR^5O$—; or $X^1$ and $X^2$ taken together are —N=$CR^6CR^6$=N—; or $X^1$ and $X^2$ taken together are —N=$CR^3NR^3$—; or $X^1$ and $X^2$ taken together are =N—O—N= or =N—S—N=; or $X^1$ and $X^2$ taken together are —O—$CR^3$=N—;

Z is O, $NR^7$, or S;

each occurrence of $R^1$ is independently H, $C_1$–$C_6$ alkyl, or $C_1$–$C_3$ fluoroalkyl, with H and $C_1$–$C_3$ alkyl being preferred;

each occurrence of $R^2$ is independently H, halogen, cyano, hydroxy, $C_1$–$C_6$ alkoxy, $C_1$–$C_3$ fluoroalkoxy, thiol, $C_1$–$C_6$ alkyl, $C_1$–$C_3$ fluoroalkyl, $C_2$–$C_6$ alkoxyalkyl, $C_6$–$C_{12}$ aryl, $C_3$–$C_{12}$ heteroaryl, $C_7$–$C_{12}$ arylalkyl, $C_4$–$C_{12}$ heteroarylalkyl, $C_6$–$C_{12}$ aryloxy, $C_7$–$C_{12}$ aryloxyalkyl, $C_7$–$C_{12}$ arylalkoxy, or $C_4$–$C_{12}$ heteroarylalkoxy, with H, halogen, cyano and alkoxy being preferred, and such that when $R^2$ is hydroxy, thiol, alkoxy, fluoroalkoxy, aryloxy, or arylalkoxy, n is 3 or 4 and such $R^2$ group is not attached to the same carbon as the Z group or the benzoxazine amide nitrogen;

each occurrence of $R^3$ and $R^7$ is independently H, $C_1$–$C_6$ alkyl, $C_1$–$C_3$ fluoroalkyl, $C_7$–$C_{12}$ arylalkyl, or $C_4$–$C_{12}$ heteroarylalkyl, with $C_1$–$C_3$ alkyl being preferred;

each occurrence of $R^4$ is independently H, $C_1$–$C_6$ alkyl, $C_1$–$C_3$ fluoroalkyl, $C_2$–$C_6$ alkoxyalkyl, $C_7$–$C_{12}$ arylalkyl, $C_4$–$C_{12}$ heteroarylalkyl, or $C_7$–$C_{12}$ aryloxyalkyl, with H, $C_1$–$C_6$ alkyl, $C_1$–$C_3$ fluoroalkyl, being preferred;

each occurrence of $R^5$ is H, halogen, cyano, $C_1$–$C_6$ alkyl, $C_1$–$C_3$ fluoroalkyl, $C_2$–$C_6$ alkoxyalkyl, $C_7$–$C_{12}$ arylalkyl, $C_4$–$C_{12}$ heteroarylalkyl, or $C_7$–$C_{12}$ aryloxyalkyl, with H, cyano, $C_1$–$C_3$ alkyl, $C_1$ fluoroalkyl, $C_7$–$C_{10}$ arylalkyl and $C_4$–$C_8$ heteroarylalkyl being preferred, and H, cyano, $C_1$–$C_3$ alkyl, and $C_1$ fluoroalkyl being more preferred;

each occurrence of $R^6$ is H, cyano, hydroxy, $C_1$–$C_6$ alkoxy, $C_1$–$C_6$ alkyl, $C_1$–$C_3$ fluoroalkyl, $C_2$–$C_6$ alkoxyalkyl, $C_7$–$C_{12}$ arylalkyl, $C_4$–$C_{12}$ heteroarylalkyl, $C_6$–$C_{12}$ aryloxy, $C_7$–$C_{12}$ aryloxyalkyl, $C_7$–$C_{12}$ arylalkoxy, or $C_4$–$C_{12}$ heteroarylalkoxy, with H, cyano, alkoxy, $C_1$–$C_3$ alkyl, and $C_1$ fluoroalkyl being preferred; and n is 2, 3 or 4.

For each of the alkyl, aryl and heteroaryl groups mentioned above with reference to Formula II, it will be understood that one or more carbon atoms in such groups may be substituted with one or more members selected from the group consisting of $C_1$–$C_3$ alkyl, $C_1$–$C_3$ alkoxy, hydroxy, halo, amino, $C_1$–$C_3$ alkylamino, or $C_1$–$C_6$ dialkylamino.

In another preferred embodiment, $X^1$ and $X^2$ taken together are —OCR$^5_2$O— or —OCH$_2$CR$^5_2$O—, and n is 2 or 3. $R^1$ is preferably H, in which case n is preferably 2.

In another preferred embodiment, $X^1$ and $X^2$ taken together are —N=CR$^6$CR$^6$=N, and n is 2 or 3. Preferably, the $R^6$ groups are independently H or $C_1$–$C_6$ alkyl. Also, $R^1$ is preferably H, in which case n is preferably 2.

In another preferred embodiment, $X^1$ and $X^2$ taken together are =N—O—N= or =N—S—N=; and n is 2 or 3. More preferably, $X^1$ and $X^2$ taken together are =NON=, and $R^1$ is H, in which case n is preferably 2.

In another embodiment, the present invention includes precursors of the compounds shown above, having the following structure:

Formula III

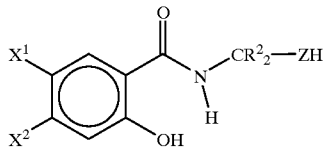

wherein, for the purposes of this structure, $X^1$, $X^2$, $R^2$, Z and n are the same as for Formula II above.

As used herein, the terms "alkyl", "alkenyl," and "alkynyl" refer to saturated and unsaturated monovalent radicals in accordance with their standard meanings, including straight-chain, branched-chain, and cyclic moieties, optionally containing one or more ring heteroatoms, such as oxygen, sulfur, and nitrogen. Exemplary cyclic moieties include cyclopentyl, cyclohexyl, tetrahydrofuranyl, pyrrolidyl, piperidyl, and morpholino.

"Lower alkyl", "lower alkenyl", and "lower alkynyl" refer to such groups containing one to six carbon atoms. Exemplary alkyl groups include methyl, ethyl, isopropyl, 2-butyl, cyclopentyl, and the like.

The term "dialkylamino" encompasses such groups wherein the two alkyl groups taken together form a 5 to 7 member ring including the amine nitrogen as one of the ring atoms, such as pyrrolidyl.

By "halogen" is meant fluoro, chloro or bromo, and preferably fluoro. The term "fluoro" is used herein to include both single and multiple fluorine substitutions, with perfluorinated $C_1$–$C_3$ moieties being preferred.

The terms "aryl" and "aromatic carbocyclic moiety" denote an aromatic ring or fused ring structure of carbon atoms with no heteroatoms in the ring(s). Examples are phenyl, naphthyl, anthracyl, and phenanthracyl. Preferred examples are phenyl and napthyl, with phenyl being most preferred. The terms "heteroaryl" and "aromatic heterocyclic moiety" are used herein to denote an aromatic ring or fused ring structure of carbon atoms with one or more non-carbon atoms, such as oxygen, nitrogen, and sulfur, in the ring, or in one or more of the rings in fused ring structures. Examples are furyl, pyranyl, thienyl, imidazyl, pyrrolyl, pyridyl, pyrazolyl, pyrazinyl, pyrimidinyl, indolyl, quinolyl, isoquinolyl, quinoxalyl, and quinazolinyl. Preferred examples are furyl, imidazyl, pyranyl, pyrrolyl, and pyridyl.

The compounds of the present invention can be synthesized in a variety of ways, using conventional synthetic chemistry techniques.

Thus, the present invention includes a method for synthesizing a benzoxazine compound in accordance with Formula I or II above. In the method, an appropriately substituted salicylic acid (i.e., containing the desired X group substitution on the phenyl ring) is activated using a carboxylic acid activating agent in the presence of an appropriate anhydrous solvent such as dichloromethane, chloroform, tetrahydrofuran, ethyl acetate, or the like. Exemplary carboxylactivating agents include carbonyldiimidazole, inorganic acid chlorides such as phosgene, and carboxylic acid anhydrides such as trifluoroacetic acid anhydride. The activated salicylic acid is then reacted with a heteroatom-substituted alkyl amine of the form NH$_2$(CR$^2_2$)$_n$ZH, where n is 2, 3 or 4, and Z is a heteroatom such as O, NHR$^7$, or S, with $R^2$ and $R^7$ defined as above, under conditions effective to form an amide adduct having the structure shown at Formula III above. For example, reaction of the activated salicylic acid with an aminoalcohol yields a Formula III compound wherein Z=O. Reaction with an aminothiol yields a compound with Z=S.

After removal of residual reactants, if desired (e.g., by silica gel chromatography), the amide adduct is reacted with a trialkylorthocarboxylate of the form RC(OR')$_3$ under conditions effective to cyclize the Z moiety, amide nitrogen, and phenolic oxygen via the central carbon atom (marked with an asterisk) of the RC*(OR')$_3$ reactant, resulting in the formation of a benzoxazine compound in accordance with Formula I or II above, where the $R^1$ moiety in Formula I or II derives from R in the RC(OR')$_3$ reactant. Preferably, the reaction is conducted in the presence of an acid catalyst such as an aryl or alkyl sulfonic acid (e.g., tosylate), trifluoroacetic acid or formic acid, in a solvent of low basicity such as chloroform or dichloromethane, for example. The benzoxazine product may be purified by standard methods, e.g., silica gel chromatography, and may be further refined by recrystallization. Preferably, the Z moiety in the benzoxazine product is O or S, and more preferably is O.

In another reaction scheme, compounds of the invention can be prepared by activating the carboxyl group of an appropriately substituted salicylic acid as above, followed by addition of an unsubstituted or substituted 2-oxazoline, 2-thiazoline, or 2-imidazoline to give the desired compound in accordance with Formula I or II.

Exemplary synthetic protocols for preparing compounds in accordance with the present invention are provided in Examples 1 through 8 below.

The above-described compounds can be incorporated into a variety of formulations (e.g., capsule, tablet, timed-release capsule, syrup, suppository, injectable form, etc.) for administration to a subject. Similarly, various modes of delivery (e.g., oral, buccal, rectal, parenteral, intraperitoneal, etc.) can be employed. Dose levels employed can vary widely, and can readily be determined by those of skill in the art. Preferred formulations of the compounds are oral preparations, particularly capsules or tablets containing each from about 1 mg up to about 100 mg of active ingredient. Depending on the strength of the compound, a typical dosage may be one 10-mg tablet taken once a day, or one time-release capsule or tablet of 100 mg taken once a day, for example. The time-release effect may be obtained by capsule materials that dissolve at different pH values, by capsules that release slowly by osmotic pressure, or by any other known means of controlled release. Subjects contemplated for treatment with the invention compounds include humans, domesticated animals, laboratory animals, and the like.

Accordingly, the invention compounds can be employed for decreasing the amount of time needed to learn a cognitive, motor or perceptual task. Alternatively, invention compounds, in suitable formulations, can be employed for increasing the time for which cognitive, motor or perceptual tasks are retained. As another alternative, invention compounds, in suitable formulations, can be employed for decreasing the quantity and/or severity of errors made in recalling a cognitive, motor or perceptual task. Such treatment may prove especially advantageous in individuals who have suffered injury to the nervous system, or who have endured disease of the nervous system, especially injury or disease which affects the number of AMPA receptors in the nervous system. Invention compounds are administered to the affected individual, and thereafter, the individual is presented with a cognitive, motor or perceptual task. The individual's performance is detectably improved as a result of administration of the compound.

Metabolically stable, positive modulators of AMPA receptors that are active in the CNS have many potential applications in humans. For example, increasing the strength of excitatory synapses can compensate for losses of synapses or receptors associated with aging and brain disease (e.g., Alzheimer's). Enhancing AMPA receptors can cause more rapid processing by multisynaptic circuitries found in higher brain regions and thus produce an increase in perceptual-motor and intellectual performance. As another example, because increasing AMPA receptor-mediated responses facilitates synaptic changes of the type believed to encode memory, the compounds of the invention may be used as memory enhancers.

Additional applications for the compounds of the present invention include restoring biochemical and synaptic balance between brain networks where an imbalance occurs due to decreased AMPA receptor currents. Such therapeutic uses include, but are not limited to, treatment of psychiatric and neurological disorders such as schizophrenia, schizophreniform behavior, other psychoses, and clinical depression.

Accordingly, invention compounds, in suitable formulations, can be employed for decreasing the amount of time needed to learn a cognitive, motor or perceptual task. Alternatively, invention compounds can be employed for increasing the time for which cognitive, motor or perceptual tasks are retained. As another alternative, invention compounds can be employed for decreasing the quantity and/or severity of errors made in recalling a cognitive, motor or perceptual task. Such treatment may prove especially advantageous in individuals who have suffered injury to the nervous system, or who have endured disease of the nervous system, especially injury or disease which affects the number of AMPA receptors in the nervous system.

The compounds of the present invention can also be used as a tool for studying the biophysical and biochemical properties of the AMPA receptor and the consequences of selectively enhancing excitatory transmission on the operation of neuronal circuitry. Because invention compounds reach central synapses, they allow for testing of the behavioral effects of enhancing AMPA receptor currents.

Studies demonstrating the ability of the compounds of the present invention to enhance AMPA receptor function, and thus enhance cognitive activities, are described in Example 9. In a first study, compounds prepared as set forth in Examples 1 to 8 were tested for their ability to enhance excitatory responses (field EPSPs) in rat hippocampal tissue. Hippocampal tissue slices were perfused with artificial cerebrospinal fluid containing increasing concentrations of test compound at 15–30 minute intervals separated by perfusion with ACSF without the test compound, and the percent increases in EPSP amplitude and half-width before and after compound perfusion were determined.

With reference to Table 1, it can be seen that the compounds of the invention exhibited significant EPSP effects, ranging from about 8% to about 35% based on compound concentrations ranging from about 5 $\mu$M to about 100 $\mu$M. For example, compound 1, wherein Z is O, R is CH, $R^0$ is $CH_2$, $R^2$ is H, and n is 2, affords an increase in EPSP response of 34% when perfused at a concentration of 30 $\mu$M. About the same activity is observed for compound 4, wherein Z is sulfur, indicating that substitution of sulfur for oxygen at this position provides activity similar to that of the oxygen-containing compound. With reference to compounds 1 and 2, expansion of the left-hand ring to six ring atoms when $R^0$ is $CH_2CH_2$ gives rise to enhanced activity, as evidenced by the 35% increase in EPSP produced by a 5 $\mu$M compound concentration, making this a preferred substitution. Good results are also obtained with compound 3, having a more bulky gem-dimethylmethyl group at the $R^0$ position, which affords a 33% increase in EPSP at a 30 $\mu$M concentration. This indicates that other substitutions can be made in this region while maintaining strong biological activity. Substitution with $CH_2$—$CH(CH_3)$ and $CH(CH_3)$ $CH_2$ moieties in the right-hand ring, relative to compound 1, affords lower EPSP responses at compound concentrations of 30 $\mu$M, indicating that these substitutions are less preferred by this assay. In particular, the presence of a methyl-substituted methylene group alpha to the amide nitrogen atom (compound 6) appears to lower activity relative to the case where the methyl-substituted methylene group is alpha to the ring oxygen (Z) (compounds 5.1 and 5.2). Substitution with a propylene chain at the $(CR^2{}_2)_n$ position (compound 7) affords somewhat better activity, relative to compounds 5.1, 5.2 and 6, although not as great as for compound 1 (ethylene). Thus, compounds wherein n=2 represent a preferred embodiment. Compound 8 (R=CCH$_3$) shows lower but still significant EPSP activity, with an observed EPSP increase of 8% at a concentration of 100 µM, indicating that more bulky substitutions at this position may exhibit lower activity.

Also included in Table 1 are data collected for an open-ring compound in accordance with formula III above, which was prepared as described in Example 1 (compound 1i). The increased EPSP response observed for this compound demonstrates that ring closure is not essential to activity.

Surprisingly, it has been found by the applicants that the compounds of the present invention, which contain a heteroatom at the Z position exhibit substantially greater activity than corresponding compounds which contain CH$_2$ at this position. In this regard, it is seen that compounds 1, 2 and 7 exhibit EPSP-enhancing activities approximately 3- to 10-fold more potent than methylene-containing analogs 1c, 2c and 7c. These results indicate that the presence of a heteroatom at the Z position is a contributing factor to the high potencies of the present compounds.

The ability of a compound to produce an increase in the EPSP response has been a reliable predictor of the ability to improve memory in the 8-arm radial maze task. The last column of Table 1 lists threshold doses of compounds that were effective to produce significant enhancement of memory in rats tested in a learning paradigm using an 8-arm radial maze as described in Staubli et al., *PNAS* 91:11158–1162 (1994).

The compounds of the present invention produce a graded dose-response in this behavioral test, as illustrated in FIG. 1 for compound 1. The left half of the figure shows the average number of correct choices before the occurrence of the first error in the retention phase of the task at three different dosages (0.03, 0.1, and 0.5 mg/kg). The right bar of each pair represents the results for the same animals administered vehicle alone on alternate days of testing. The right half of the figure shows the average number of total errors observed following administration of a given compound dosage (left-hand bar of each data pair) compared to vehicle alone (right-hand bar of each data pair). As can be seen, administration of compound 1 at dosages of 0.03, 0.1, and 0.5 mg/kg consistently affords a significant, dose-dependent increase in the average number of correct choices before the first error, relative to appropriate controls, as well as a significant, dose-dependent reduction in the average total number of errors.

Further data obtained using this memory test are shown in the right-most column of Table 1. As can be seen, compounds in accordance with the invention show high potency by this method, with compounds 1 and 2 showing minimum effective doses (MEDs) of 50 and 10 µg/kg, respectively. Also, it can be seen that the compounds of the invention show significantly higher memory-enhancing activities (10- to 20-fold greater) than analogs containing methylene in place of oxygen at the Z position (comparing compounds 1 and 2 with 1c and 2c), corroborating the EPSP results.

The compounds of formulas I and II are chiral by virtue of the chiral carbon linking the O, N and Z moieties together, and bearing the R$^1$ substituent. On account of their different stereoisomeric configurations, the enantiomers will not necessarily have the same biological activities. In accordance with another aspect of the invention, it has been found by the applicants that the chiral compounds of formulas I and II, which are typically synthesized in racemic form, are resolvable into their constituent enantiomers, which in fact have different biological activities.

Thus, the present invention includes a method for separating the stereoisomers of the chiral compounds of the invention (Formulas I and II) by making use of their differential retention on a stationary chiral support. In the method, the racemic or diastereomeric mixture is dissolved in an appropriate solvent of low eluting strength, which will vary dependent upon the solute and the stationary phase and can be determined by those skilled in the art, and applied to a suitable column that is packed with an appropriated chiral stationary phase. The individual isomers are then eluted from the column through the use of a solvent composition suitable to cause differential elution of the isomers. The eluted isomers may be reapplied to the same or different column in order to further enhance the resolution if not sufficient, or may be applied to a stationary support contained in a simulated moving bed apparatus of higher efficiency. An exemplary stationary chiral support is given in Example 10 below. Also, since it is possible that the order of elution of the enantiomers may vary depending on the structure of the particular compound being resolved, and the nature of the selected stationary phase, the activity of each resolved enantiomer should be determined by the methods described in Example 9, or any other suitable method, to determine the relative potencies of the resolved enantiomers.

Example 10 illustrates the different biological activities of the enantiomers of the invention using compound 1 by way of example. As detailed in Example 10, racemic compound 1 (Example 1) was loaded onto a chiral HPLC column (Daicel 20×200 mm Chiralpak AD) using a mobile phase of 70:30 ethanol/hexane until loading was complete. The mobile phase was then changed to 70:30 2-propanol/hexane for 55 minutes at 3 mL/min, followed by 80:20 2-propanol/hexane. The first enantiomer eluted with a retention time of about 61 min, and the second, after 82 minutes. The resolved enantiomers were further purified by crystallization and then tested by the methods described in Example 9.

With reference to Table 2 (Example 10), it is seen that most or all of the observed biological activity for compound 1 resides in only one of the enantiomers, i.e., the first-eluting enantiomer under the conditions described in Example 10. Moreover, the first-eluting enantiomer is significantly more potent than the racemic form. Specifically, the first-eluting enantiomer exhibits an EPSP increase of 80% when present at 50 µM (Table 2), while the racemic mixture shows an increase of 34% at a concentration of 30 µM (Table 1). Conversely, the second-eluting enantiomer does not detectably change the EPSP response when present at a concentration of 50 µM (Table 2). These results are reinforced by results from the maze test discussed in Example 9. The active enantiomer of compound 1 affords an MED of 10 µg/kg, whereas the MED of the less active enantiomer is 50-fold higher (500 µg/kg), though there is still a beneficial memory effect.

Accordingly, the treatment methods of the invention may employ an enantiomerically enriched form of the disclosed compounds consisting predominantly or virtually exclusively of the more biologically active form, thereby increasing the potency (on a mass basis) of the compound administered. In a preferred embodiment, the more active enantiomer is present with an enantiomeric excess of at least 80% (i.e., a ratio of more active enantiomer to less active enantiomer of greater than 9:1). Using the methodology described in Example 10, resolved R and S enantiomers of the compounds of the invention are routinely obtained in greater than 99% enantiomeric purity (98% enantiomeric excess). In addition, administration of the more active enantiomer may also improve the side-effect profile of the compound. Conversely, the less active enantiomer can be used in varying proportions and amounts as a diluent to offset metabolic degradation or modification of the more active form in vivo. For example, if the administered compound is cleared too rapidly from the blood stream, an increased amount of the less active enantiomer can be administered to lessen the clearance of the more active form. Thus, the invention contemplates the use of the less active enantiomer in excess over the more active form. In particular, the invention contemplates a compound of the invention having an enantiomeric excess of the less active enantiomer of at least 80%. The relative proportions of the two enantiomers appropriate for a given indication may also depend on the possible inhibitory effect on receptor binding that the less active enantiomer may have on the more active enantiomer.

From the foregoing, it can be seen how the objects and advantages of the invention are met. The invention provides compounds that are useful for enhancing brain receptor synaptic responses, and find utility in a varieity of therapeutic applications. The compounds are useful as antidepressants, and for improving the strength and duration of memory. The compounds are also useful for improving sensory-motor problems, and for alleviating psychoses such as schizophrenia and schizophreniform behavior. In addition, the compounds are readily synthesized by conventional chemical methods, and can be resolved into separate stereoisomers if desired.

The following examples are offered for purposes of illustration only and are not intended to limit the scope of the invention in any way.

EXAMPLE 1

7,8-Dihydro-5aH, 10H-1,3-dioxolo[4,5-g]oxazolo[2,3-b][1,3]benzoxazin-10-one (1)

Synthesis was begun with the preparation of 3,4-methylenedioxysalicylic acid from sesamol and carbon dioxide according to the well-known Kolbe-Schmitt reaction as follows. Sesamol (5.0 g, 36 mmol) was dissolved in 20 mL anhydrous diglyme in a 250-mL high-pressure apparatus (Parr Instruments Co.) and treated with 1.44 g (36.0 mmol) of 60% sodium hydride. Stirring was continued for 20 min, after which the apparatus was pressurized to 700 psi with carbon dioxide and heated to 190° C. for 8 hr. The apparatus was cooled to ambient and the carbon dioxide was vented. The reaction mixture was diluted with 50 mL diethyl ether and acidified with 10% hydrochloric acid (10 mL). Further dilution of the mixture with 500 mL diethyl ether and transfer to a separatory funnel generated an aqueous layer, which was removed and extracted with diethyl ether. The organic layers were combined and exhaustively extracted with saturated sodium bicarbonate. The bicarbonate solutions were combined, acidified with 10% hydrochloric acid, and thoroughly extracted with diethyl ether. The diethyl ether extracts were combined, washed with saturated sodium chloride, and dried over anhydrous sodium sulfate. Concentration of the dry solution (in vacuo) gave 4.5 g (68%) 3,4-methylenedioxysalicylic acid as a beige solid. Infrared (IR) spectroscopy (thin film): 2869, 2351, 1637, 1478, 1442, 1419, 1240, 1194, 1124, 1036, 930, 854, and 692 $cm^{-1}$ 3,4-Methylenedioxysalicylic acid was also synthesized by the following alternate method. Sesamol (7.00 g; 50.7 mmol), carbon tetrachloride (10.0 g; 65.0 mmol), copper powder (20 mg), and 30 mL 48% (w/v) sodium hydroxide solution were mixed at room temperature and then refluxed for 8 hr. The basic solution was treated as above to yield 5.0 g (53%) of the salicylate as a beige solid.

4,5-Methylenedioxysalicylic acid (2.215 g; 12.17 mmol) from either of the two procedures described above was suspended in 25 mL $CH_2Cl_2$, to which was added 2.06 g (4.6% excess) carbonyldiimidazole. Carbon dioxide was evolved and the solution quickly became homogeneous. After 4.5 h, the solution of activated salicylate was added, with stirring, over a 5 min period to 1.65 g (about 2 equivalents) of ethanolamine in 30 mL $CH_2Cl_2$, which caused a dark oil to separate from the solution. The reaction was quenched by addition of 1.4 mL (2 equivalents) of acetic acid and the resulting N-hydroxyethylsalicylamide was purified by silica gel chromatography. The product (compound 1i) was eluted with hexane/ethyl acetate/ethanol (40/66/4) following a side product that amounted to 175 mg. The main product fractions were concentrated on a rotary evaporator and diluted with pet ether. The resulting white, flocculent precipitate was collected by filtration and dried in vacuo. Yield from the first crop was 2.06 g. A second crop gave 115 mg, or a total yield of 79%. Mp=140.8–142.0° C.; UV/Visible Spectra: neutral form (PhOH)$\lambda_{max}$=318 nm; ionized form (PhO)$\lambda_{max}$=342 nm. IR (KBr): —OH and —NH stretch at 3410 and 3360 $cm^{-1}$; amide carbonyl at 1640 and 1610 (strong) $cm^{-1}$. $^1$HNMR (200 MHz; CDCl$_3$/d$_6$DMSO): δ 12.89 (1H, s); 7.7 (1H, br s); 7.212 (1H, s); 6.426 (1H, s); 5.944 (2H, s); 4.245 (1H, t, J=6 Hz); 3.75 (2H, m); and 3.53 ppm (2H, m) downfield from tetramethylsilane (TMS).

2-(2-Hydroxy-4,5-methylenedioxybenzamido)ethanol (8.9 g; 40 mmol) was suspended in 320 mL dry chloroform, to which trimethylorthoformate (32 mL, 290 mmol) and formic acid (7.8 mL, 170 mmol) were added. The suspension was heated to reflux for 2.5 hours and diluted with ethyl acetate. The diluted solution was washed with a sodium bicarbonate buffer (pH 10), followed by a saturated sodium chloride solution and finally, dried over anhydrous sodium sulfate. The solution was evaporated onto silica gel and purified by multiple flash chromatographic steps on silica gel (ethyl acetate/hexane=1:1 or diethyl ether/hexane=9:1). Subsequent isolation of intermediate byproducts and treatment with formic acid yielded a total of 4.78 g (51%); after recrystallization from methylene chloride/diethyl ether) of (R,S)-7,8-dihydro-5aH, 10H-1,3-dioxolo[4,5-g]oxazolo[2,3-b][1,3]benzoxazin-10-one with mp=152–153° C. IR (thin film): 2899, 1667, 1460, 1420, 1260, 1117, 1034, and 926 $cm^{-1}$. $^1$HNMR (500 MHz; CDCl$_3$): δ 7.27 (1H, s), 6.53 (1H, s), 6.18 (1H, s), 6.015 (2H, AB quartet), 4.30 (1H, td, J=7 & 1.2 Hz), 4.22–4.28 (1H, m), 4.20 (1H, ddd, J=10, 7 & 1.4 Hz), and 3.55–3.60 ppm (1H, m.

EXAMPLE 2

8,9-Dihydro-6aH, 11H-1,4-dioxan[2,3-g]oxazolo[2,3-b][1,3]benzoxazin-11-one (2)

Synthesis was begun with the preparation of 4,5-ethylenedioxysalicylic acid from 6-hydroxy-1,4-benzodioxan and carbon dioxide according to the procedure described above in Method 1, with the modification that 95% sodium hydride was used, the pressure of carbon dioxide was 900 psi, and the temperature was 245° C. The product acid was obtained as a beige solid in 52% yield. IR (thin film): 3072, 2975, 2876, 2656, 2546, 1680, 1573, 1415, 1299, 1258, 1186, 1061, 897, and 747 $cm^{-1}$.

4,5-Ethylenedioxysalicylic acid was converted into (R,S)-8,9-dihydro-6aH, 11H-1,4-dioxan[2,3-g]oxazolo[2,3-b][1,3]benzoxazin-11-one by the procedure described above in Example 1 to yield a white solid. Mp=215–216° C. IR (thin film): 2899, 1670, 1626, 1470, 1306, 1121, 1062, and 929 cm$^{-1}$. $^1$HNMR (200 MHz; CDCl$_3$): δ 7.40 (1H, s), 6.56 (1H, s), 6.17 (1H, s), 4.1–4.5 (7H, m), and 3.5–3.8 ppm (1H, m).

EXAMPLE 3

7,8-Dihydro-2,2-dimethyl-5aH, 10H-1,3-dioxolo[4,5-g]oxazolo[2,3-b][1,3]benzoxazin-10-one (3)

2,2-Dimethyl-5-hydroxybenzo[1,3]dioxole was treated with carbon dioxide to provide the corresponding salicylic acid as described in Example 2 above and was obtained in 41% yield as a beige solid. The salicylic acid was converted into (R,S)-7,8-Dihydro-2,2-dimethyl-5aH, 10H-1,3-dioxolo[4,5-g]oxazolo[2,3-b][1,3]benzoxazin-10-one as described in Example 2 above to yield a white solid with mp=212–214° C. IR (thin film): 1664, 1466, 1415, 1266, 1117, 1062, 983, and 743 cm$^{-1}$. $^1$HNMR (200 MHz; CDCl$_3$): δ 7.18 (1H, s), 6.44 (1H, s), 6.17 (1H, s), 41–4.4 (3H, m), 3.4–3.8 (1H, m), and 1.69 ppm (6H, s).

EXAMPLE 4

7,8-Dihydro-5aH, 10H-1,3-dioxolo[4,5-g]thiazolo[2,3-b][1,3]benzoxazin-10-one (4)

Synthesis of the title compound was conducted as in Example 1 except that aminoethanethiol (generated in situ from the hydrochloride salt by the action of 3 equivalents of triethylamine) was substituted for aminoethanol to yield a white solid with mp=149–150° C. IR (thin film): 2899, 1670, 1626, 1470, 1420, 1306, 1121, 1062, and 929 cm$^{-1}$. $^1$HNMR (200 MHz; CDCl$_3$): δ 7.29 (1H, s), 6.49 (1H, s), 6.46 (1H, s), 6.015 (2H, s), 4.66 (1H, ddd, J=12.0, 6.0 & 1.1 Hz), 3.66 (1H, td, J=11.4 & 5.9 Hz), 3.33 (1H, td, J=11.4 & 5.9 Hz), and 1H, ddd, J=12.0, 5.9 & 1.1 Hz)

EXAMPLE 5

7,8-Dihydro-7-methyl-5aH, 10H-1,3-dioxolo[4,5-g]oxazolo[2,3-b][1,3]benzoxazin-10-one (5)

4,5-Methylenedioxysalicylic acid was activated by carbonyldiimidazole in methylene chloride and combined with 1-amino-2-propanol in essentially an identical manner as for Example 1 above. An acidic quench and subsequent purification by flash chromatography (SiO$_2$) using (1:1) hexane-ethyl acetate gave 1-(2-hydroxy-4,5-methylenedioxybenzamido)-2-propanol as a waxy white solid in 67% yield.

1-(2-Hydroxy-4,5-methylenedioxybenzamido)-2-propanol (440 mg; 1.8 mmol) was suspended in 15 mL dry chloroform, to which 2.0 mL (18 mmol) trimethylorthoformate and 0.75 mL (16 mmol) formic acid were added. The reaction mixture was heated to reflux for 2 h, concentrated in vacuo onto silica gel, and purified by flash chromatography (SiO$_2$) using (3:1) hexane-ethyl acetate to yield 259 and 61 mg of the first and second diastereomeric fractions, respectively, and 68 mg unresolved material for a total yield of 85%

Fraction 1: Mp=148–150° C. IR (thin film) 1677, 1472, 1433, 1269, 1120, and 1048 cm$^{-1}$. $^1$H NMR (300 MHz; CDCl$_3$): δ 7.26 (1H, s), 6.52 (1H, s) 6.18 (1H, s) 6.00 (2H, AB quartet,), 4.55–4.65 (1H, m), 4.23 (1H, dd, J=3.1 & 6.4 Hz), 3.13 (1H, t, J=6 Hz), and 1.46 ppm (3H, d, J=4 Hz).

Fraction 2: Mp 105–106° C. IR (thin film): 1672, 1467, 1424, 1263, 1123, and 1035 cm$^{-1}$. $^1$H NMR (300 MHz; CDCl$_3$): δ 7.26 (1H, s), 6.52 (1H, s), 6.19 (1H, s), 6.01 (2H, AB quartet), 4.60–4.71 (1H, m), 3.79–3.83 (1H, m), 3.72–3.77 (1H, m), and 1.47 ppm (3H, d, 4.8 Hz).

EXAMPLE 6

7,8-Dihydro-8-methyl-5aH, 10H-1,3-dioxolo[4,5-g]oxazolo[2,3-b][1,3]benzoxazin-10-one (6)

4,5-Methylenedioxysalicylic acid was activated by carbonyldiimidazole in methylene chloride and combined with 2-amino-1-propanol in essentially an identical manner as for Example 1 above. An acidic quench and subsequent purification by flash chromatography (SiO$_2$) using (1:1) hexane-ethyl acetate gave 2-(2-hydroxy-4,5-methylenedioxybenzamido)-1-propanol as a waxy white solid in 52% yield.

2-(2-Hydroxy-4,5-methylenedioxybenzamido)-1-propanol was treated with trimethylorthoformate and formic acid as in Example 5 above to give a colorless oil (84% yield), which solidified to a glass. IR (thin film): 1670, 1630, 1466, 1418, 1262, 1124, and 1033 cm$^{-1}$. $^1$H NMR (300 MHz; CDCl$_3$): δ 7.25 (1H, s), 6.51 (1H, s), 6.23 (1H, s), 6.00 (2H, AB quartet), 4.54 (1H, p, J=1.8 Hz), 4.36 (1H, dd, J=3 & 6 Hz), 3.92 (1H, J=6 Hz), and 1.40 ppm (3H, d, J=6 Hz).

EXAMPLE 7

8,9-Dihydro-5aH, 7H, 10H-1,3-dioxolo[4,5-g][1,3]oxazino[2,3-b][1,3]benzoxazin-11-one (7)

4,5-Methylenedioxysalicylic acid was activated by carbonyldiimidazole in methylene chloride and combined with 3-aminopropanol in essentially an identical manner as for Example 1 above. An acidic quench and subsequent purification by flash chromatography (SiO$_2$) using (1:1) hexane-ethyl acetate gave 3-(2-hydroxy-4,5-methylenedioxybenzamido)-1-propanol as a waxy white solid in 64% yield.

3-(2-Hydroxy-4,5-methylenedioxybenzamido)-1-propanol was treated with trimethylorthoformate and formic acid as in Example 5 above to give a white solid in 78% yield with transitions at 162–168° C. (glass) and 174–175° C. (melt). IR (thin film): 1659, 1464, 1283, 1263, 1155, 1036, 1014, and 934 cm$^{-1}$. $^1$H NMR (300 MHz; CDCl$_3$) δ 7.31 (1H, s), 7.49 (1H, s), 6.08 (1H, s), 6.00 (2H, AB quartet), 4.60–4.80 (1H, ddm, J=5.2 & 13.5 Hz), 4.15–4.30 (1H, dm, J=11.9 Hz), 3.99 (1H, td, 3.3 & 11.6 Hz), 2.95–3.10 (1H, td, 4.1 & 13 Hz), 1.90–2.10 (1H, m ), and 1.50–1.65 ppm (1H, m).

EXAMPLE 8

7,8-Dihydro-5a-methyl-10H-1,3-dioxolo[4,5-g]oxazolo[2,3-b][1,3]benzoxazin-10-one (8)

4,5-Methylenedioxysalicylic acid (0.472 g; 2.59 mmol) was suspended in 8 mL dry chloroform to which was added 0.476 g (4.00 mmol) thionyl chloride. The reaction mixture was heated at reflux for 3 h, during which time the suspension turned into a dark solution. The solution was allowed to cool to ambient and the solvent and excess thionyl chloride were removed in vacuo. The residue was dissolved in 8 mL methylene chloride and 0.392 g (4.60 mmol) 2-methyl-2-oxazoline was added dropwise. The solution was stirred for 1 h and then concentrated onto silica gel for subsequent purification by column chromatography (hexane/ethyl acetate=2:1) to yield 0.500 g of crude product. The product was recrystallized from ethyl acetate/hexane (1:10) to give 0.392 g (64% yield) of white crystalline solid with mp 132–133° C. IR (thin film): 1659, 1629, 1454, 1376, and 1267 cm$^{-1}$. $^1$H NMR (500 MHz; CDCl$_3$) δ 7.28 (1H, s), 6.48 (1H, s), 6.00 (2H, AB quartet), 4.27 (1H, dd, J=10.5 & 5.6 Hz), 4.17–4.23 (1H, m), 4.05–4.13 (1H, m), 3.55 (1H, td, J=10.6 & 6.5 Hz), and 1.59 ppm (3H, s).

EXAMPLE 9

Physiological Testing

The physiological effects of compounds in accordance with the invention can be tested in vitro with slices of rat hippocampus according to the following procedure. Excitatory responses (field EPSPs) are measured in hippocampal slices, which are maintained in a recording chamber continuously perfused with artificial cerebrospinal fluid (ACSF). During a 15–30 minute interval, the perfusion medium is switched to one containing various concentrations of the test compounds. Responses collected immediately before and at the end of drug perfusion were superimposed in order to calculate both the percent increase in EPSP amplitude and percent increase in the width of the response at one-half the peak height (half-width). An increase in either measure, that is, of the amplitude or half-width, can be used as an indicator of beneficial therapeutic activity.

To conduct these tests, the hippocampus was removed from anesthetized, 2 month old Sprague-Dawley rats and tissue slices (400 micrometers thick) were prepared and maintained in an interface chamber at 35° C. using conventional techniques [see, for example, Dunwiddie and Lynch, *J. Physiol.* 276: 353–367 (1978)]. The chamber was constantly perfused at 0.5 mL/min with ACSF containing (in mM): NaCl 124, KCl 3, KH$_2$PO$_4$ 1.25, MgSO$_4$ 2.5, CaCl$_2$ 3.4, NaHCO$_3$ 26, glucose 10 and L-ascorbate 2. A bipolar nichrome stimulating electrode was positioned in the dendritic layer (stratum radiatum) of the hippocampal subfield CA1 close to the border of subfield CA3.

Current pulses (0.1 msec) through the stimulating electrode activate a population of the Schaffer-commissural (SC) fibers, which arise from neurons in the subdivision CA3 and terminate in synapses on the dendrites of CA1 neurons. Activation of these synapses causes them to release the transmitter glutamate. Glutamate binds to the post-synaptic AMPA receptors which then transiently open an associated ion channel and permit a sodium current to enter the postsynaptic cell. This current results in a voltage in the extracellular space (the field excitatory post-synaptic potential or field "EPSP") which is recorded by a high impedance recording electrode positioned in the middle of the stratum radiatum of CA1.

For the experiments summarized in Table 1, the intensity of the stimulation current was adjusted to produce half-maximal EPSPs (typically about 1.5–2.0 mV). Paired stimulation pulses were given every 40 sec with an interpulse interval of 200 msec (see below). The field EPSPs of the second response were digitized and analyzed to determine amplitude, half-width, and response area. If the responses were stable for 15–30 minutes (baseline), test compounds were added to the perfusion lines for a period of about 20 minutes. The perfusion was then changed back to regular ACSF.

Paired-pulse stimulation was used because stimulation of the SC fibers, in part, activates interneurons that generate an inhibitory postsynaptic potential (IPSP) in the pyramidal cells of CA1. This feed forward IPSP typically sets in after the EPSP reaches its peak. It accelerates the repolarization and shortens the decay phase of the EPSP, and thus could partially mask the effects of the test compounds. One of the relevant features of the feed-forward IPSP is that it can not be reactivated for several hundred milliseconds following a stimulation pulse. This phenomenon can be employed to advantage to eliminate IPSP by delivering paired pulses separated by 200 milliseconds and using the second ("primed") response for data analysis.

The field EPSP recorded in field CA1 after stimulation of CA3 axons is known to be mediated by AMPA receptors: the receptors are present in the synapses [Kessler et al., *Brain Res.* 560: 337–341 (1991)] and drugs that selectively block the receptor selectively block the field EPSP [Muller et al., *Science* 242:1694–1697 (1988)]. Aniracetam increases the mean open time of the AMPA receptor channel and as expected from this increases the amplitude of the synaptic current and prolongs its duration [Tang et al., *Science* 254:288–290 (1991)]. These effects are mirrored in the field EPSP, as reported in the literature [see, for example, Staubli et al., *Psychobiology*, supra; Xiao et al., *Hippocampus* supra; Staubli et al., *Hippocampus* 2: 49–58 (1992)]. Similar results have been reported for previously disclosed benzamide derivatives of aniracetam [International Publication No. WO 94/02475].

Compounds of the invention were assayed in the physiological test system described above, with the results presented in Table 1 below. The first data column shows the concentration of each test compound from a representative experiment that produced the increase in EPSP response (which results from increased AMPA receptor currents) that is given in the second data column as the percent increase in amplitude of the EPSP response. The compounds of the invention produce dose-dependent increases and are effective at concentrations as low as 5 μM. Also included in Table 1 are results for the ring-open amide intermediate (compound 1i) leading to compound 1 (see Example 1), and three analog compounds containing CH$_2$ at position Z (compounds 1c, 2c, and 7c).

The ability of a compound to produce an increase in the EPSP response has been a reliable predictor of the ability to improve memory in the 8-arm radial maze task. The last column of Table 1 describes the threshold dose for enhancing memory in rats that were tested in a learning paradigm using an 8-arm radial maze as described in Staubli et al., *PNAS* 91:11158–1162 (1994). A graded dose-response is produced in the behavioral task test, as illustrated in FIG. 1 for compound 1. All of the data in FIG. 1 were obtained using the same group of ten rats. On alternate days, the rats were given a single dose of vehicle (saline) or drug (compound 1), after which the rats were tested in the maze task. In other words, vehicle alone was administered to the group on days 1, 3 and 5, and compound at a selected dosage was administered on days 2 and 4. The results represent the average error rates observed (number correct before first error on left side of figure, total number of errors on right side of figure) for the group at a given dosage of compound averaged from days 2 and 4 (left-hand bar in each data pair) or following administration of vehicle alone averaged from days 3 and 5 (right hand bar in each data pair). Error bars indicate the standard error of the mean (SEM). The asterisks (*) in the figure indicate data wherein p<0.05 by the paired t test.

It is noteworthy that substitution of a heteroatom, such as oxygen or sulfur, for a methylene group at the Z position imparts increased potency in both the EPSP response and maze assays (compare compounds 1, 2, and 7 with compounds 1c, 2c, and 7c, respectively, in Table 1).

TABLE 1

Biological Activities

[Structure diagram of benzoxazine compound with R⁰, R, Z, and (CR²₂)ₙ substituents]

| Compound | R | R⁰ | (CR²₂)ₙˣ | Z | Concentration ($\mu$M) | EPSP Response (%) | Maze MED† ($\mu$g/kg) |
|---|---|---|---|---|---|---|---|
| 1 | CH | CH₂ | (CH₂)₂ | O | 30 | 34 | 50 |
| 1c* | CH | CH₂ | (CH₂)₂ | CH₂ | 100 | 25 | 1000 |
| 1i | — | CH₂ | (CH₂)₂ | —OH | 100 | 8 | NT‡ |
| 2 | CH | C₂H₄ | (CH₂)₂ | O | 5 | 35 | 10 |
| 2c* | CH | C₂H₄ | (CH₂)₂ | CH₂ | >30 | 25 | 100 |
| 3 | CH | CMe₂ | (CH₂)₂ | O | 30 | 33 | NT |
| 4 | CH | CH₂ | (CH₂)₂ | S | 30 | 20 | NT |
| 5.1 | CH | CH₂ | CH₂CHMe | O | 30 | 14 | NT |
| 5.2 | CH | CH₂ | CH₂CHMe | O | 30 | 10 | NT |
| 6 | CH | CH₂ | CHMeCH₂ | O | 100 | 10 | NT |
| 7 | CH | CH₂ | (CH₂)₃ | O | 30 | 15 | NT |
| 7c* | CH | CH₂ | (CH₂)₃ | CH₂ | 300 | 25 | NT |
| 8 | CCH₃ | CH₂ | (CH₂)₂ | O | 100 | 8 | NT |

†Minimum Effective Dose;
ˣleft-most carbon is linked to amide nitrogen and right-most carbon is linked to Z;
‡NT = not tested;
*included for comparison with compounds of the present invention

EXAMPLE 10

Enantiomeric Resolution of Benzoxazines

Samples of benzoxazines can be resolved on a chiral stationary phase column (Daicel Chiralpak AD column) using HPLC. As a nonlimiting example, compound 1 (225 mg) was dissolved in 0.9 mL of ethanol with warming and sonication. The sample was applied to the column while a mobile phase composed of 70:30 ethanol/hexane was flowing at 1 mL/min. After the entire sample had been applied to the column, the flow rate was increased to 3 mL/min. After 35 min the mobile phase was changed to 70:30 2-propanol/hexane and after 55 min to 80:20 2-propanol/hexane. The first enantiomer eluted with a retention time of about 61 min and the second after approximately 82 min. Material from the first fraction was crystallized from methylene chloride and diethyl ether to give 103 mg (91% recovery). The second enantiomer was similarly recovered and recrystallized. The absolute configurations of the resolved enantiomers were not determined. The resolved enanteriomers of compound 1 were tested by the methods described in Example 9. The results are shown in Table 2 below.

TABLE 2

Activities of Enantiomers of Compound 1

| Column Fraction | Concentration ($\mu$M) | EPSP Response (%) | Maze MED† ($\mu$g/kg) |
|---|---|---|---|
| 1 | 50 | 80 | 10 |
| 2 | 50 | 0 | 500 |

†Minimum Effective Dose

While the invention has been described in detail with reference to particular embodiments, it will be understood that various variations and modifications can be made without departing from the spirit of the invention.

We claim:

1. A compound having one of the following structures:

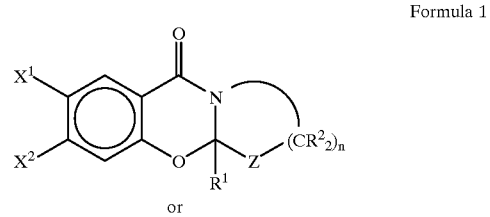

Formula 1 or

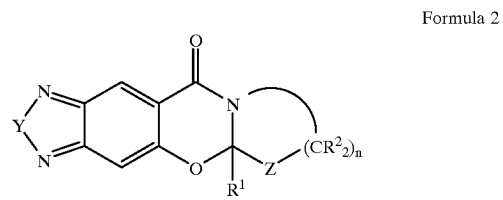

Formula 2 wherein:

$X^1$ and $X^2$ are independently selected from H, $NR^3{}_2$, $-OR^4$, and $-CH_2OR^4$; or $X^1$ and $X^2$ taken together are $-OCR^5{}_2O-$, $-OCR^5{}_2CR^5{}_2O-$; or $-OCR^5=CR^5O-$; or $X^1$ and $X^2$ taken together are $-N=CR^6CR^6=N-$; or $X^1$ and $X^2$ taken together are $-N=CR^3NR^3-$; or $X^1$ and $X^2$ taken together are $-O-CR^3=N-$; or Y is O or S;

Z is O, $NR^7$, or S;

each occurrence of $R^1$ is independently H, $C_1$–$C_6$ alkyl, or $C_1$–$C_3$ fluoroalkyl, each occurrence of $R^2$ is independently H, halogen, cyano, hydroxy, $C_1$–$C_6$ alkoxy, $C_1$–$C_3$ fluoroalkoxy, thiol, $C_1$–$C_6$ alkyl, $C_1$–$C_3$ fluoroalkyl, $C_2$–$C_6$ alkoxyalkyl, $C_6$–$C_{12}$ aryl, $C_3$–$C_{12}$ heteroaryl, $C_7$–$C_{12}$ arylalkyl, $C_4$–$C_{12}$ heteroarylalkyl, $C_6$–$C_{12}$ aryloxy, $C_7$–$C_{12}$ aryloxyalkyl, $C_7$–$C_{12}$ arylalkoxy, or $C_4$–$C_{12}$ heteroarylalkoxy;

each occurrence of $R^3$ and $R^7$ is independently H, $C_1$–$C_6$ alkyl, $C_1$–$C_3$ fluoroalkyl, $C_7$–$C_{12}$ arylalkyl or $C_4$–$C_{12}$ heteroarylalkyl;

each occurrence of $R^4$ is independently H, $C_1$–$C_6$ alkyl, $C_1$–$C_3$ fluoroalkyl, $C_2$–$C_6$ alkoxyalkyl, $C_7$–$C_{12}$ arylalkyl, $C_4$–$C_{12}$ heteroarylalkyl, or $C_7$–$C_{12}$ aryloxyalkyl;

each occurrence of $R^5$ is H, halogen, cyano, $C_1$–$C_6$ alkyl, $C_1$–$C_3$ fluoroalkyl, $C_2$–$C_6$ alkoxyalkyl, $C_7$–$C_{12}$ arylalkyl, $C_4$–$C_{12}$ heteroarylalkyl, or $C_7$–$C_{12}$ aryloxyalkyl;

each occurrence of $R^6$ is H, cyano, hydroxy, $C_1$–$C_6$ alkoxy, $C_1$–$C_6$ alkyl, $C_1$–$C_3$ fluoroalkyl, $C_2$–$C_6$ alkoxyalkyl, or $C_7$–$C_{12}$ arylalkyl, $C_4$–$C_{12}$ heteroarylalkyl, $C_6$–$C_{12}$ aryloxy, $C_7$–$C_{12}$ aryloxyalkyl, $C_7$–$C_{12}$ arylalkoxy, or $C_4$–$C_{12}$ heteroarylalkoxy; and n is 2, 3 or 4.

2. A compound in accordance with claim 1, wherein the compound has the structure shown at Formula 1; $X^1$ and $X^2$ taken together are —$OCR^5_2O$— or —O—$CH_2CR^5_2O$—; and n is 2 or 3.

3. A compound in accordance with claim 2, wherein $R^1$ is H.

4. A compound in accordance with claim 3, wherein n is 2.

5. A compound in accordance with claim 1, wherein the compound has the structure shown at Formula 1; $X^1$ and $X^2$ taken together are —N=$CR^6CR^6$=N—; and n is 2 or 3.

6. A compound in accordance with claim 5, wherein $R^1$ is H.

7. A compound in accordance with claim 6, wherein n is 2.

8. A compound in accordance with claim 1, wherein the compound has the structure shown at Formula 2; Y is O or S; and n is 2 or 3.

9. A compound in accordance with claim 8, wherein the compound has the structure shown at Formula 2, Y is O; and $R^1$ is H.

10. A compound in accordance with claim 9, wherein n is 2.

11. A compound in accordance with claim 1, having the structure 7,8-dihydro-5aH, 10H-1,3-dioxolo[4,5-g]oxazolo[2,3-b][1,3]benzoxazin-10-one.

12. A compound in accordance with claim 1, having the structure 8,9-dihydro-6aH, 11H-1,4-dioxan[2,3-g]oxazolo[2,3-b][1,3]benzoxazin-11-one.

13. A compound in accordance with claim 1, having the structure 7,8-dihydro-2,2-dimethyl-5aH, 10H-1,3-dioxolo[4,5-g]oxazolo[2,3-b][1,3]benzoxazin-10-one.

14. A compound in accordance with claim 1, having an enantiomeric excess of greater than 80%.

15. A method of preparing a compound in accordance with claim 1, having an enantiomeric excess of greater than 80%, said method comprising:

applying a compound having the structure shown in claim 1 to a stationary chiral support, eluting a first enantiomer of said compound under selected conditions effective to retain the second enantiomer of said compound on the chiral support until substantially all of said first enantiomer has been eluted, and optionally eluting said second enantiomer from the chiral support, whereby each eluted enantiomer is obtained in enantiomeric excess of greater than 80%.

16. A method for the treatment of a human subject to enhance synaptic response mediated by AMPA receptors, said method comprising administering to said subject an effective amount of a compound having one of the following structures:

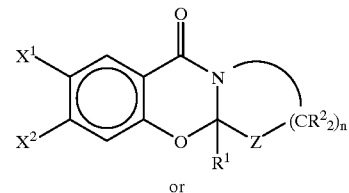

Formula 1 or

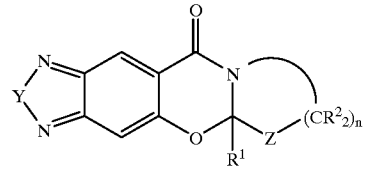

Formula 2 wherein:

$X^1$ and $X^2$ are independently selected from H, $NR^3_2$, —$OR^4$, and —$CH_2OR^4$; or $X^1$ and $X^2$ taken together are —$OCR^5_2O$—, —$OCR^5_2CR^5_2O$—, or —$OCR^5$=$CR^5O$—; or $X^1$ and $X^2$ taken together are —N=$CR^6CR^6$=N—; or $X^1$ and $X^2$ taken together are —N=$CR^3NR^3$—; or $X^1$ and $X^2$ taken together are —O—$CR^3$=N—; or Y is O or S;

Z is O, $NR^7$, or S;

each occurrence of $R^1$ is independently H, $C_1$–$C_6$ alkyl, or $C_1$–$C_3$ fluoroalkyl, each occurrence of $R^2$ is independently H, halogen, cyano, hydroxy, $C_1$–$C_6$ alkoxy, $C_1$–$C_3$ fluoroalkoxy, thiol, $C_1$–$C_6$ alkyl, $C_1$–$C_3$ fluoroalkyl, $C_2$–$C_6$ alkoxyalkyl, $C_6$–$C_{12}$ aryl, $C_3$–$C_{12}$ heteroaryl, $C_7$–$C_{12}$ arylalkyl, $C_4$–$C_{12}$ heteroarylalkyl, $C_6$–$C_{12}$ aryloxy, $C_7$–$C_{12}$ aryloxyalkyl, $C_7$–$C_{12}$ arylalkoxy, or $C_4$–$C_{12}$ heteroarylalkoxy;

each occurrence of $R^3$ and $R^7$ is independently H, $C_1$–$C_6$ alkyl, $C_1$–$C_3$ fluoroalkyl, $C_7$–$C_{12}$ arylalkyl or $C_4$–$C_{12}$ heteroarylalkyl;

each occurrence of $R^4$ is independently H, $C_1$–$C_6$ alkyl, $C_1$–$C_3$ fluoroalkyl, $C_2$–$C_6$ alkoxyalkyl, $C_7$–$C_{12}$ arylalkyl, $C_4$–$C_{12}$ heteroarylalkyl, or $C_7$–$C_{12}$ aryloxyalkyl;

each occurrence of $R^5$ is H, halogen, cyano, $C_1$–$C_6$ alkyl, $C_1$–$C_3$ fluoroalkyl, $C_2$–$C_6$ alkoxyalkyl, $C_7$–$C_{12}$ arylalkyl, $C_4$–$C_{12}$ heteroarylalkyl, or $C_7$–$C_{12}$ aryloxyalkyl;

each occurrence of $R^6$ is H, cyano, hydroxy, $C_1$–$C_6$ alkoxy, $C_1$–$C_6$ alkyl, $C_1$–$C_3$ fluoroalkyl, $C_2$–$C_6$ alkoxyalkyl, or $C_7$–$C_{12}$ arylalkyl, $C_4$–$C_{12}$ heteroarylalkyl, $C_6$–$C_{12}$ aryloxy, $C_7$–$C_{12}$ aryloxyalkyl, $C_7$–$C_{12}$ arylalkoxy, or $C_4$–$C_{12}$ heteroarylalkoxy; and n is 2, 3 or 4.

17. A method for the treatment of schizophrenia, schizophreniform behavior, or depression in a human subject, said method comprising administering to a human subject in need of such treatment a compound in a therapeutically effective amount, said compound having one of the following structures:

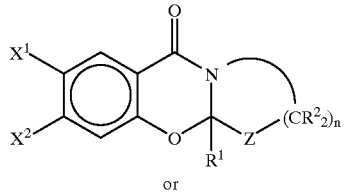

Formula 1 or

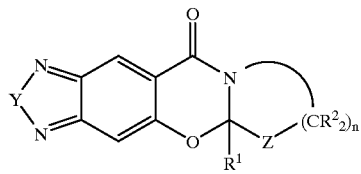

Formula 2 wherein:

$X^1$ and $X^2$ are independently selected from H, $NR^3{}_2$, $-OR^4$, and $-CH_2OR^4$; or $X^1$ and $X^2$ taken together are $-OCR^5{}_2O-$, $-OCR^5{}_2CR^5{}_2O-$, or $-OCR^5=CR^5O-$; or $X^1$ and $X^2$ taken together are $-N=CR^6CR^6=N-$; or $X^1$ and $X^2$ taken together are $-N=CR^3NR^3-$; or $X^1$ and $X^2$ taken together are $-O-CR^3=N-$; or Y is O or S;

Z is O, $NR^7$, or S;

each occurrence of $R^1$ is independently H, $C_1$–$C_6$ alkyl, or $C_1$–$C_3$ fluoroalkyl, each occurrence of $R^2$ is independently H, halogen, cyano, hydroxy, $C_1$–$C_6$ alkoxy, $C_1$–$C_3$ fluoroalkoxy, thiol, $C_1$–$C_6$ alkyl, $C_1$–$C_3$ fluoroalkyl, $C_2$–$C_6$ alkoxyalkyl, $C_6$–$C_{12}$ aryl, $C_3$–$C_{12}$ heteroaryl, $C_7$–$C_{12}$ arylalkyl, $C_4$–$C_{12}$ heteroarylalkyl, $C_6$–$C_{12}$ aryloxy, $C_7$–$C_{12}$ aryloxyalkyl, $C_7$–$C_{12}$ arylalkoxy, or $C_4$–$C_{12}$ heteroarylalkoxy;

each occurrence of $R^3$ and $R^7$ is independently H, $C_1$–$C_6$ alkyl, $C_1$–$C_3$ fluoroalkyl, $C_7$–$C_{12}$ arylalkyl or $C_4$–$C_{12}$ heteroarylalkyl;

each occurrence of $R^4$ is independently H, $C_1$–$C_6$ alkyl, $C_1$–$C_3$ fluoroalkyl, $C_2$–$C_6$ alkoxyalkyl, $C_7$–$C_{12}$ arylalkyl, $C_4$–$C_{12}$ heteroarylalkyl, or $C_7$–$C_{12}$ aryloxyalkyl;

each occurrence of $R^5$ is H, halogen, cyano, $C_1$–$C_6$ alkyl, $C_1$–$C_3$ fluoroalkyl, $C_2$–$C_6$ alkoxyalkyl, $C_7$–$C_{12}$ arylalkyl, $C_4$–$C_{12}$ heteroarylalkyl, or $C_7$–$C_{12}$ aryloxyalkyl;

each occurrence of $R^6$ is H, cyano, hydroxy, $C_1$–$C_6$ alkoxy, $C_1$–$C_6$ alkyl, $C_1$–$C_3$ fluoroalkyl, $C_2$–$C_6$ alkoxyalkyl, or $C_7$–$C_{12}$ arylalkyl, $C_4$–$C_{12}$ heteroarylalkyl, $C_6$–$C_{12}$ aryloxy, $C_7$–$C_{12}$ aryloxyalkyl, $C_7$–$C_{12}$ arylalkoxy, or $C_4$–$C_{12}$ heteroarylalkoxy; and n is 2, 3 or 4.

18. A method in accordance with claim 17, wherein said compound is administered to alleviate schizophrenia or schizophreniform behavior.

19. A method in accordance with claim 17, wherein said compound is administered to alleviate depression.

20. A method for strengthening the memory of a human subject, comprising administering to a human subject in need of such treatment a compound in an amount effective to increase the duration or accuracy of the subject's memory and/or decrease the amount of time needed for a subject to learn a cognitive, motor or perceptual task, said compound having one of the following structures:

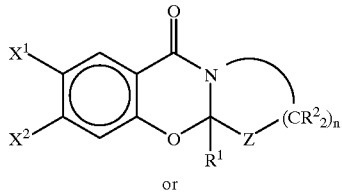

Formula 1 or

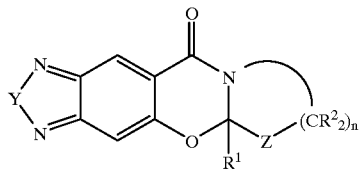

Formula 2 wherein:

$X^1$ and $X^2$ are independently selected from H, $NR^3{}_2$, $-OR^4$, and $-CH_2OR^4$; or $X^1$ and $X^2$ taken together are $-OCR^5{}_2O-$, $-OCR^5{}_2CR^5{}_2O-$, or $-OCR^5=CR^5O-$; or $X^1$ and $X^2$ taken together are $-N=CR^6CR^6=N-$; or $X^1$ and $X^2$ taken together are $-N=CR^3NR^3-$; or $X^1$ and $X^2$ taken together are $-O-CR^3=N-$; or Y is O or S;

Z is O, $NR^7$, or S;

each occurrence of $R^1$ is independently H, $C_1$–$C_6$ alkyl, or $C_1$–$C_3$ fluoroalkyl, each occurrence of $R^2$ is independently H, halogen, cyano, hydroxy, $C_1$–$C_6$ alkoxy, $C_1$–$C_3$ fluoroalkoxy, thiol, $C_1$–$C_6$ alkyl, $C_1$–$C_3$ fluoroalkyl, $C_2$–$C_6$ alkoxyalkyl, $C_6$–$C_{12}$ aryl, $C_3$–$C_{12}$ heteroaryl, $C_7$–$C_{12}$ arylalkyl, $C_4$–$C_{12}$ heteroarylalkyl, $C_6$–$C_{12}$ aryloxy, $C_7$–$C_{12}$ aryloxyalkyl, $C_7$–$C_{12}$ arylalkoxy, or $C_4$–$C_{12}$ heteroarylalkoxy;

each occurrence of $R^3$ and $R^7$ is independently H, $C_1$–$C_6$ alkyl, $C_1$–$C_3$ fluoroalkyl, $C_7$–$C_{12}$ arylalkyl or $C_4$–$C_{12}$ heteroarylalkyl;

each occurrence of $R^4$ is independently H, $C_1$–$C_6$ alkyl, $C_1$–$C_3$ fluoroalkyl, $C_2$–$C_6$ alkoxyalkyl, $C_7$–$C_{12}$ arylalkyl, $C_4$–$C_{12}$ heteroarylalkyl, or $C_7$–$C_{12}$ aryloxyalkyl;

each occurrence of $R^5$ is H, halogen, cyano, $C_1$–$C_6$ alkyl, $C_1$–$C_3$ fluoroalkyl, $C_2$–$C_6$ alkoxyalkyl, $C_7$–$C_{12}$ arylalkyl, $C_4$–$C_{12}$ heteroarylalkyl, or $C_7$–$C_{12}$ aryloxyalkyl;

each occurrence of $R^6$ is H, cyano, hydroxy, $C_1$–$C_6$ alkoxy, $C_1$–$C_6$ alkyl, $C_1$–$C_3$ fluoroalkyl, $C_2$–$C_6$ alkoxyalkyl, or $C_7$–$C_{12}$ arylalkyl, $C_4$–$C_{12}$ heteroarylalkyl, $C_6$–$C_{12}$ aryloxy, $C_7$–$C_{12}$ aryloxyalkyl, $C_7$–$C_{12}$ arylalkoxy, or $C_4$–$C_{12}$ heteroarylalkoxy; and n is 2, 3 or 4.

21. A method in accordance with claim 16, wherein the compound has the structure shown at Formula 1; $X^1$ and $X^2$ taken together are $-OCR^5{}_2O-$ or $-O-CH_2CR^5{}_2O-$; and n is 2 or 3.

22. A method in accordance with claim 16, wherein the compound has the structure shown at Formula 1; $X^1$ and $X^2$ taken together are $-N=CR^6CR^6=N-$; and n is 2 or 3.

23. A method in accordance with claim 16, wherein the compound has the structure shown at Formula 2; Y is O or S; and n is 2 or 3.

24. A method in accordance with claim 16, wherein the compound has the structure 7,8-dihydro-5aH, 10H-1,3-dioxolo[4,5-g]oxazolo[2,3-b][1,3]benzoxazin-10-one.

25. A method in accordance with claim 16, wherein the compound has the structure 8,9-dihydro-6aH, 11H-1,4-dioxan[2,3-g]oxazolo[2,3-b][1,3]benzoxazin-11-one.

26. A method in accordance with claim 16, wherein the compound has the structure 7,8-dihydro-2,2-dimethyl-5aH, 10H-1,3-dioxolo[4,5-g]oxazolo[2,3-b][1,3]benzoxazin-10-one.

27. A method in accordance with claim 16, wherein the compound has an enantiomeric excess of greater than 80%.

28. A method in accordance with claim 17, wherein the compound has the structure shown at Formula 1; $X^1$ and $X^2$ taken together are —$OCR^5_2O$— or —O—$CH_2CR^5_2O$—; and n is 2 or 3.

29. A method in accordance with claim 17, wherein the compound has the structure shown at Formula 1; $X^1$ and $X^2$ taken together are —N=$CR^6CR^6$=N—; and n is 2 or 3.

30. A method in accordance with claim 17, wherein the compound has the structure shown at Formula 2; Y is O or S; and n is 2 or 3.

31. A method in accordance with claim 17, wherein the compound has the structure 7,8-dihydro-5aH, 10H-1,3-dioxolo[4,5-g]oxazolo[2,3-b][1,3]benzoxazin-10-one.

32. A method in accordance with claim 17, wherein the compound has the structure 8,9-dihydro-6aH, 11H-1,4-dioxan[2,3-g]oxazolo[2,3-b][1,3]benzoxazin-11-one.

33. A method in accordance with claim 17, wherein the compound has the structure 7,8-dihydro-2,2-dimethyl-5aH, 10H-1,3-dioxolo[4,5-g]oxazolo[2,3-b][1,3]benzoxazin-10-one.

34. A method in accordance with claim 17, wherein the compound has an enantiomeric excess of greater than 80%.

35. A method in accordance with claim 20, wherein the compound has the structure shown at Formula 1; $X^1$ and $X^2$ taken together are —$OCR^5_2O$— or —O—$CH_2CR^5_2O$—; and n is 2 or 3.

36. A method in accordance with claim 20, wherein the compound has the structure shown at Formula 1; $X^1$ and $X^2$ taken together are —N=$CR^6CR^6$=N—; and n is 2 or 3.

37. A method in accordance with claim 20, wherein the compound has the structure shown at Formula 2; Y is O or S; and n is 2 or 3.

38. A method in accordance with claim 20, wherein the compound has the structure 7,8-dihydro-5aH, 10H-1,3-dioxolo[4,5-g]oxazolo[2,3-b][1,3]benzoxazin-10-one.

39. A method in accordance with claim 20, wherein the compound has the structure 8,9-dihydro-6aH, 11H-1,4-dioxan[2,3-g]oxazolo[2,3-b][1,3]benzoxazin-11-one.

40. A method in accordance with claim 20, wherein the compound has the structure 7,8-dihydro-2,2-dimethyl-5aH, 10H-1,3-dioxolo[4,5-g]oxazolo[2,3-b][1,3]benzoxazin-10-one.

41. A method in accordance with claim 20, wherein the compound has an enantiomeric excess of greater than 80%.

* * * * *